(12) United States Patent
Tenn, III

(10) Patent No.: US 10,035,756 B2
(45) Date of Patent: Jul. 31, 2018

(54) INTEGRATED PROCESS FOR NITRILE MANUFACTURE WITH ENHANCED LIQUID-LIQUID EXTRACTION

(71) Applicant: INVISTA NORTH AMERICA S.A.R.L., Wilmington, DE (US)

(72) Inventor: William J. Tenn, III, Beaumont, TX (US)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 83 days.

(21) Appl. No.: 15/320,904

(22) PCT Filed: Jun. 25, 2015

(86) PCT No.: PCT/US2015/037686
§ 371 (c)(1),
(2) Date: Dec. 21, 2016

(87) PCT Pub. No.: WO2015/200630
PCT Pub. Date: Dec. 30, 2015

(65) Prior Publication Data
US 2017/0152211 A1 Jun. 1, 2017

Related U.S. Application Data

(60) Provisional application No. 62/018,125, filed on Jun. 27, 2014.

(51) Int. Cl.
*C07C 209/48* (2006.01)
*C07C 253/10* (2006.01)
*C07C 253/34* (2006.01)

(52) U.S. Cl.
CPC .......... *C07C 209/48* (2013.01); *C07C 253/10* (2013.01); *C07C 253/34* (2013.01)

(58) Field of Classification Search
None
See application file for complete search history.

(56) References Cited

U.S. PATENT DOCUMENTS 3,496,215 A 2/1970 Drinkard et al.
3,496,217 A 2/1970 Drinkard, Jr. et al.
(Continued)

FOREIGN PATENT DOCUMENTS

WO 2001/036429 A1 5/2001
WO 2012/005917 A1 1/2012
(Continued)

OTHER PUBLICATIONS

International Search Report and Written Opinion Received for PCT Application No. PCT/US2015/037686, dated Nov. 12, 2015, 9 pages.
(Continued)

*Primary Examiner* — Sudhakar Katakam
*Assistant Examiner* — Jennifer C Sawyer

(57) ABSTRACT

Phosphorus-containing ligands are recovered from mixtures comprising 3-pentenenitrile (3PN) and adiponitrile (ADN), using liquid-liquid extraction. ADN is produced by hydrocyanation of 3PN. The ADN is hydrogenated to produce a hexamethyiene diamine (HMD) and at least one byproduct including bis-hexamethylene triamine (BHMT) or 1,2-diaminocyclohexane. At least a portion of the HMD product or byproduct is used to enhance the liquid-liquid extraction to recover phosphorus-containing ligand.

14 Claims, 3 Drawing Sheets

(56) References Cited

U.S. PATENT DOCUMENTS

| | | |
|---|---|---|
| 3,496,218 A | 2/1970 | Drinkard, Jr. |
| 3,696,153 A | 10/1972 | Kershaw et al. |
| 3,758,584 A | 9/1973 | Bivens et al. |
| 3,773,809 A | 11/1973 | Walter |
| 3,986,985 A | 10/1976 | Dewdney et al. |
| 4,082,811 A | 4/1978 | Shook, Jr. |
| 4,339,395 A | 7/1982 | Barnette et al. |
| 5,105,015 A | 4/1992 | Lin et al. |
| 5,512,695 A | 4/1996 | Kreutzer et al. |
| 5,512,696 A | 4/1996 | Kreutzer et al. |
| 5,523,453 A | 6/1996 | Breikss |
| 5,543,536 A | 8/1996 | Tam |
| 5,663,369 A | 9/1997 | Kreutzer et al. |
| 5,688,986 A | 11/1997 | Tam et al. |
| 5,693,843 A | 12/1997 | Breikss et al. |
| 5,723,641 A | 3/1998 | Tam et al. |
| 5,847,101 A | 12/1998 | Okayama et al. |
| 5,959,135 A | 9/1999 | Garner et al. |
| 6,120,700 A | 9/2000 | Foo et al. |
| 6,171,996 B1 | 1/2001 | Garner et al. |
| 6,171,997 B1 | 1/2001 | Foo |
| 6,376,714 B1 | 4/2002 | Allgeier et al. |
| 6,399,534 B2 | 6/2002 | Bunel et al. |
| 6,924,345 B2 | 8/2005 | Gagne et al. |
| 6,936,171 B2 | 8/2005 | Jackson et al. |
| 7,935,229 B2 | 5/2011 | Deckert et al. |
| 2013/0211126 A1 | 8/2013 | Moerbe et al. |

FOREIGN PATENT DOCUMENTS

| | | |
|---|---|---|
| WO | 2013/053610 A1 | 4/2013 |
| WO | 2014/099607 A1 | 6/2014 |
| WO | 2015/200630 A1 | 12/2015 |

OTHER PUBLICATIONS

International Preliminary Report on Patentability Received for PCT Patent Application No. PCT/US2015/037686, dated Jan. 5, 2017, 7 pages.

INTEGRATED PROCESS FOR NITRILE MANUFACTURE WITH ENHANCED LIQUID-LIQUID EXTRACTION

FIELD OF THE INVENTION

The invention relates to the production of hexamethylene diamine (HMD) and the recovery of catalyst and ligand from a hydrocyanation reaction product mixture comprising adiponitrile using liquid-liquid extraction.

BACKGROUND OF THE INVENTION

It is well known in the art that complexes of nickel with phosphorous-containing ligands are useful as catalysts in hydrocyanation reactions. Such nickel complexes using monodentate phosphites are known to catalyze hydrocyanation of butadiene to produce a mixture of pentenenitriles. These catalysts are also useful in the subsequent hydrocyanation of pentenenitriles to produce adiponitrile, an important intermediate in the production of nylon. It is further known that bidentate phosphite, phosphinite and phosphonite ligands can be used to form nickel-based catalysts to perform such hydrocyanation reactions.

U.S. Pat. No. 3,773,809 describes a process for the recovery of Ni complexes of organic phosphites from a product fluid containing organic nitriles produced by hydrocyanating an ethylenically unsaturated organic mononitrile such as 3-pentenenitrile through extraction of the product fluid with a paraffin or cycloparaffin hydrocarbon solvent. Similarly, U.S. Pat. No. 6,936,171 to Jackson and McKinney discloses a process for recovering diphosphite-containing compounds from streams containing dinitriles.

U.S. Pat. No. 4,339,395 describes the formation of an interfacial rag layer during extended periods of continuous extraction of certain phosphite ligands. The '395 patent notes that the interfacial rag hinders, if not halts, the phase separation. Because the process is operated continuously, the rag must be removed continuously from the interface as it accumulates to avoid interrupting operation. To solve this problem for the disclosed components, the '395 patent discloses the addition of minor amounts of substantially water-free ammonia.

U.S. Pat. No. 7,935,229 describes a process for extractively removing heterogeneously dissolved catalyst from a reaction effluent of a hydrocycanation of unsaturated mononitriles to dinitriles with a hydrocarbon. The catalyst comprises a ligand which may be a monophosphite, a diphosphite, a monophosphonite or a diphosphonite. Ammonia or an amine may be added to a mixture of liquid phases before phase separation takes place.

A mixing section of a liquid-liquid extractor forms an intimate mixture of unseparated light and heavy phase. This intimate mixture comprises an emulsion phase. The emulsion phase may or may not comprise particulate solid material. This emulsion phase separates into a light phase and a heavy phase in a settling section. Accordingly, a settling section will contain at least some emulsion phase located between the upper light phase and the lower heavy phase. This emulsion phase tends to reduce in size over time. However, in some instances settling takes longer than desired or the emulsion phase never fully separates into a light phase and a heavy phase.

Addition of Lewis base, such as water, ammonia or amine, to the feed to a liquid-liquid extractor may result in enhanced settling of the emulsion phase. For example, this addition may result in the reduction of the size of the emulsion phase in the settling section, wherein the size of the emulsion phase is based upon the size of the emulsion phase in the absence of addition of Lewis base. Enhanced settling in the settling section may also be measured as art increased rate of settling, based upon the rate of settling in the absence of addition of Lewis base.

Another problem, which may be solved by addition of Lewis base, is formation of rag and build-up of a rag layer the settling section. Rag formation is discussed in U.S. Pat. No. 4,339,395 and U.S. Pat. No. 7,935,229. Rag comprises particulate solid material, and may be considered to be a form of an emulsion phase, which is particularly stable in the sense that it does not dissipate in a practical amount of time for conducting an extraction process. Rag may form in the mixing section or the settling section of an extraction stage. In the settling section, the rag forms a layer between the heavy phase and the light phase. The formation of a rag layer in the settling section inhibits proper settling of the heavy phase and the light phase. The formation of a rag layer may also inhibit the extraction of phosphorus-containing ligand from the heavy phase into the light phase. In a worst case scenario, rag can build up to the extent of completely filling a separation section, necessitating shut down of the extraction process to clean out the settling section. Addition of Lewis base to the mixing section may reduce or eliminate the size of a rag layer or reduce its rate of formation, based upon the size and rate of formation of the rag layer in the absence of addition of Lewis base.

Processes for the hydrogenation of compounds comprising nitrile groups to amine and aminonitrile compounds are known. Hydrogenation of dinitriles to the corresponding diamines is a process which has been used for a long time, in particular the hydrogenation of adiponitrile to hexamethylene diamine, a basic material in the preparation of nylon-6,6.

There has been an increasing interest in recent years in the hydrogenation (also sometimes known as semihydrogenation) of aliphatic dinitriles to aminonitriles, in particular the hydrogenation of adiponitrile to 6-aminocapronitrile, resulting either directly, or via caprolactam, in nylon-6.

U.S. Pat. No. 3,758,584 to Bivens et al. discloses a process for the catalytic hydrogenation of adiponitrile to hexamethylene diamine in the presence of a catalyst derived from a cobalt or iron compound, such as iron oxide, which has been activated in a mixture of hydrogen and ammonia at a temperature in the range of about 300° C. to about 600° C.

When a dinitrile is hydrogenated to form a diamine unwanted byproducts may be produced. For example, when adiponitrile is hydrogenated to form hexamethylene diamine, unwanted byproducts may include bis-hexamethylene triamine and diaminocyclohexane.

SUMMARY OF THE INVENTION

There are problems associated with various Lewis bases, when used in an effort to enhance phase separation. For example, water may cause hydrolysis of water sensitive ligands, such as diphosphite or diphosphonite ligands. Ammonia forms a complex with Lewis acids, which is partially soluble in the raffinate phase of extraction process. This complex has been found to promote the cyclization reaction of adiponitrile to form 2-cyanocyclopentylidinimine (CPI), when the raffinate is subjected to distillation conditions involved in the separation of adiponitrile from the raffinate phase. Other Lewis base additives, such as pyridine, should be avoided for safety reasons. Pyridine is a teratogenic substance.

In accordance with embodiments described herein, it has been discovered that polyamines are particularly advantageous, when used as Lewis base additives. Under extraction conditions discussed herein, the polyamines tend to form a complex with Lewis acid, which is solid and readily separates into the raffinate phase. Furthermore, this solid precipitate tends to be sufficiently dispersed in the raffinate phase to flow with the raffinate phase throughout the stages of a countercurrent multistage liquid-liquid extraction process. Although this complex does tend to catalyze the formation of 2-cyanocyclopentylidinimine from adiponitrile under certain distillation conditions, it can readily be removed from the raffinate phase from a countercurrent multistage liquid-liquid extraction process, e.g., by filtration, before the raffinate phase is subjected to such distillation conditions. It has further been found that bis-hexamethylene triamine is a particularly useful Lewis base additive in extraction processes described herein.

Facilities exist which produce both adiponitrile and hexamethylene diamine in a single location. Adiponitrile is produced by a hydrocyanation reaction, and hexamethylene diamine is produced by hydrogenation of the adiponitrile. In such facilities, it desirable to use the polyamine product and byproducts of the hydrogenation to enhance phase separation in the process for making adiponitrile. It especially desirable to make use of byproducts of the hydrogenation reaction by using one or more of these byproducts to enhance phase separation.

A process for making hexamethylene diamine comprises steps (i) to (viii).

In step (i), 3-pentenenitrile (3PN), hydrogen cyanide (HCN), zero valent nickel, at least one diphosphite-containing or diphosphonite-containing compound and a Lewis acid are introduced into a hydrocyanation reaction zone.

In step (ii), the hydrocyanation reaction zone of step (i) is maintained under conditions sufficient to convert 3PN and HCN to adiponitrile (ADN).

In step (iii), a product stream is withdrawn from the hydrocyanation reaction zone of step (ii). The product stream comprises 3PN, ADN, zero valent nickel, at least one diphosphite-containing or diphosphonite-containing compound and a Lewis acid. In step (iv), at least a portion of the product stream of step (iii) is contacted with an extraction solvent under conditions to obtain a mixture of product from step (iii) and extraction solvent. In step (iv) this mixture of product from step (iii) and extraction solvent is also maintained under conditions to obtain a two phase mixture comprising a light phase and a heavy phase. This light phase comprises extraction solvent and at least one diphosphite-containing or diphosponite-containing compound. The heavy phase comprises 3PN and ADN. In step (v), ADN is recovered from the heavy phase from step (iv).

In step (vi), ADN from step (v) is reacted with hydrogen to produce hexamethylene diamine (HMD) as a product amine and at least one byproduct amine selected from the group consisting of bis-hexamethylene triamine (BHMT) and 1,2-diaminocyclohexane.

In step (vii), at least one of the product amine or byproduct amines from step (vi) is contacted with product of step (iii) either before or during step (iv).

When step (vii) comprises contacting at least one of the product amine or byproduct amines from step (vi) with the product of stream of step (iii) before step (iv), solids may be removed from the product stream prior to step (iv). When step (vii) comprises contacting at least one of the product amine or byproduct amines from step (vi) with product of step (iii) during step (iv), solids may be removed from the heavy phase of step (iv).

Step (v) may comprise removing extraction solvent and pentenenitrile from the heavy phase of step (iv). Solids may be removed from the heavy phase after step (iv) and before extraction solvent is removed from the heavy phase.

Hexamethylene diamine (HMD), bis-hexamethylene triamine (BHMT) and 1,2-diaminocyclohexane from step (vi) may be separated from one another, for example, by distillation. Hexamethylene diamine (HMD), bis-hexamethylene triamine (BHMT) and 1,2-diaminocyclohexane may be used individually or collectively in step (vii). Hexamethylene diamine (HMD), which is separated from bis-hexamethylene triamine (BHMT) and 1,2-diaminocyclohexane, may be used in step (vii). Bis-hexamethylene triamine (BHMT), which is separated from hexamethylene diamine (HMD) and 1,2-diaminocyclohexane, may be used in step (vii). 1,2-Diaminocyclohexane, which is separated from bis-hexamethylene triamine (BHMT) and hexamethylene diamine (HMD), may be used in step (vii).

The Lewis acid may comprise, for example, $ZnCl_2$ or triphenylboron, $(C_6H_5)_3B$.

Step (iv) may take place in a multistage countercurrent liquid-liquid extractor. The first stage of the multistage countercurrent liquid-liquid extractor may take place in an extraction column or in a mixer-settler. The multistage countercurrent liquid-liquid extractor may comprise at least three mixer-settlers connected in series.

DETAILED DESCRIPTION OF THE INVENTION

The processes of the present invention involve methods for recovering phosphorus-containing ligand from a mixture comprising phosphorus-containing ligand and organic dinitriles, using liquid-liquid extraction.

Figure 1:
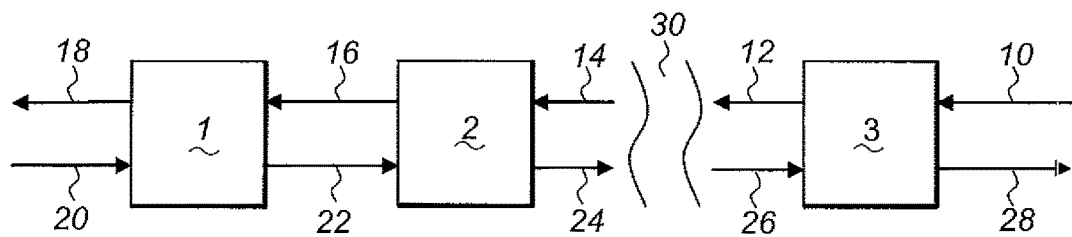
FIG. 1 is a diagram showing the flow of fluids through a multistage countercurrent liquid-liquid extractor.

FIG. 1 is a diagram of a multistage countercurrent liquid-liquid extractor. Lines in FIG. 1 represent flow of materials, rather than any particular type of equipment, such as pipes. Similarly, squares in this diagram represent stages or sections for mixing and settling, rather than any particular type of equipment.

Three stages are depicted in FIG. 1. The first stage is depicted by mixing and settling section 1. The second stage is depicted by mixing and settling section 2. The final stage is depicted by mixing and settling section 3. Gap 30 represents a space where additional stages may be inserted. For example, one or more, for example, from one to four, mixing and settling sections may be inserted in gap 30 between mixing and settling section 2 and mixing and settling section 3.

In FIG. 1, mixing and settling section 1 and mixing and settling section 3 represent the terminal mixing and settling sections of the multistage countercurrent liquid-liquid extractor. According to terminology used herein, mixing and settling section 1 represents the first terminal mixing and settling section, and mixing and settling section 3 represents the second terminal mixing and settling section.

In FIG. 1, a fresh extraction solvent feed, for example, cyclohexane, is introduced into the multistage countercurrent extractor via line 10. The extraction solvent or light phase exiting from mixing and settling section 3 passes through line 12 to the next stage of the multistage extractor. In a multistage countercurrent liquid-liquid extractor having three stages, extraction solvent in line 12 would pass directly into stage 2 via line 14. Extraction solvent from stage 2 passes through line 16 to stage 1. The extraction solvent comprising extracted phosphorus-containing compounds passes out of the stage 1 mixing and settling section through line 18.

A feed comprising phosphorus-containing ligand is fed into the stage 1 mixing and settling section via line 20. The feed further comprises a mixture comprising organic mononitriles and dinitriles, which is immiscible with the extraction solvent. The feed further comprises a Lewis acid. In stage 1, a portion of the phosphorus-containing ligand is extracted into the extraction solvent which exits stage 1 via line 18. The immiscible dinitrile and mononitrile mixture or the heavy phase is removed from the stage 1 mixing and settling section by line 22 and is passed into the stage 2 mixing and settling section. A portion of the phosphorus-containing ligand is extracted into the light phase in the stage 2 mixing and settling section. The heavy phase exits the stage 2 mixing and settling section by line 24. Similarly, if there are additional stages in gap 30 shown in FIG. 1, extraction of phosphorus-containing ligand will take place in such intermediate stages in a similar manner to that taking place in stage 2.

After the heavy phase passes through the first stage and any intermediate stages, it passes through the final stage mixing and settling section 3. In particular, the heavy phase is introduced into mixing and settling section 3 through line 26. After passing through the final stage mixing and settling section 3, the heavy phase exits via line 28.

Thus, it can be seen that the multistage countercurrent liquid-liquid extractor comprises three or more stages with countercurrent flow of extraction solvent and heavy phase. In view of the direction of flow of light and heavy phase through the stages of extraction, it will be appreciated that the concentration of solute, e.g., phosphorus-containing ligand, is highest in both the light and heavy phases of the first stage and lowest in the light and heavy phases of the final stage.

For example, the extraction solvent feed from the second stage of the countercurrent multistage extraction zone may comprise at least 1000 ppm, for example, from 2000 to 5000 ppm, of phosphorus-containing ligand. The extraction solvent feed from the second stage may comprise at least 10 ppm, for example, from 20 to 200 ppm, of nickel. At least one stage of the extraction may be carried out above 40° C. The extraction solvent may comprise, for example, cyclohexane.

Figure 2:
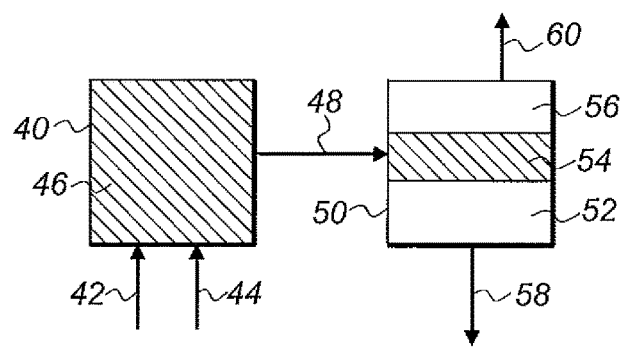
FIG. 2 is a diagram showing a mixing section and a settling section of a stage of a multistage countercurrent liquid-liquid extractor.

FIG. 2 is a diagrammatic representation of one type of an apparatus for use as a mixing and settling section. This type of apparatus is referred to herein as a mixer-settler. This mixer-settler may be used in any of the stages shown in FIG. 1. This mixer-settler comprises a mixing section 40 and a settling section 50. The mixing section 40 and the settling section 50 are separate. All of the effluent from the mixing section 40 flows into the settling section 50. Fluid from the mixing section 40 flows through the settling section 50 in a horizontal manner, although there is also no restriction of movement of fluids vertically throughout the settling section 50.

An extraction solvent is introduced into the mixing section 40 by line 42. A feed comprising phosphorus-containing ligand is introduced into the mixing section 40 by line 44. Alternatively, the contents of lines 42 and 44 may be combined upstream of the mixing section 40 and introduced into mixing section 40 through a single inlet. These two feeds are mixed in the mixing section 40 to provide a mixed phase comprising an emulsion phase represented in FIG. 2 by shaded area 46.

Line 48 represents the flow of mixed phase 46 from the mixing section 40 into the settling section 50. As depicted in FIG. 2, there are three phases in the settling section 50, including a heavy phase 52, a mixed phase 54, and a light phase 56. The heavy phase 52 is depleted in phosphorus-containing ligand, insofar as it has a lower concentration of phosphorus-containing ligand as compared with the concentration of phosphorus-containing ligand in feed 44, due to the extraction of phosphorus-containing ligand into the light phase 56. Correspondingly, the light phase 56 is enriched in phosphorus-containing ligand, insofar as it has a higher concentration of phosphorus-containing ligand as compared with the concentration of phosphorus-containing ligand in extraction solvent feed 42, due to the extraction of phosphorus-containing ligand into the light phase 56. At least a portion of the heavy phase 52 exits the settling section 50 via line 58. At least a portion of the light phase 56 is removed from the settling section 50 via line 60.

Although not shown in FIG. 2, which diagrammatically shows the flow of fluids, it will be understood that each of the mixing section 40 and the settling section 50 may comprise one or more stages, subsections, compartments or chambers. For example, settling section 50 may include more than one chamber between the point of introduction of the mixed phase 46 through line 48 and the point of withdrawal of heavy phase and light phase through lines 58 and 60. Horizontal extension between the point of introduction of the mixed phase 46 through line 48 and the point of withdrawal of heavy and light phases through lines 58 and 60 promotes settling of the light and heavy phases 56 and 52. The size of the mixed phase 54 may become progressively smaller as fluids settle and flow through the chamber. For example, the final chamber from where fluids are removed may include little or no mixed phase 54. It will further be understood that mixing section 40 may include one or more types of mixing apparatus, such as an impeller, not shown in FIG. 2.

Figure 3:
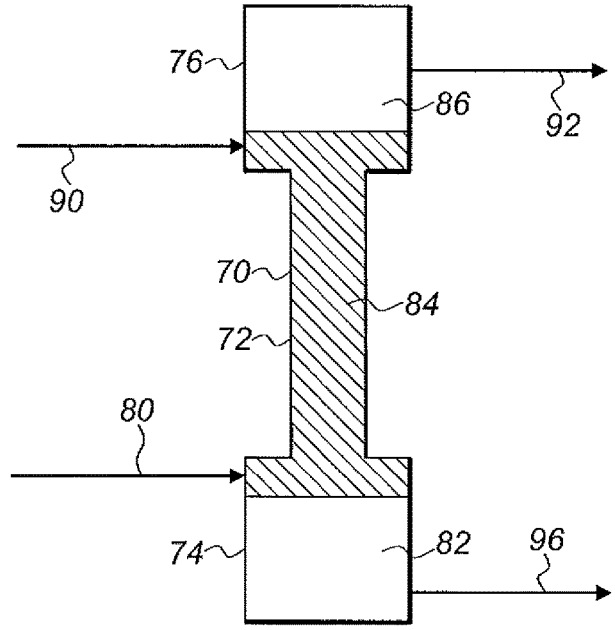
FIG. 3 is a diagram showing an extraction column.

FIG. 3 provides a representation of another type of extraction apparatus. The type of apparatus 70 shown in FIG. 3 is referred to herein as an extraction column. This extraction column 70 includes a mixing section 72, a heavy phase collection section 74 and a light phase collection section 76. The entire column 70 may be considered to be a settling section with a mixing section between collection section 74 and collection section 76. In extraction column 70 the mixing section 72 is part of the settling section. An extraction solvent is introduced into column 70 through line 80. A heavier phase comprising a phosphorus-containing ligand is introduced into column 70 through line 90. As the light phase passes upward through the column, and the heavy phase passes downward through the column, a mixture of the two phases is formed in mixing section 72. This mixture is represented in FIG. 3 as shaded mixed phase 84. This mixed phase 84 may comprise an emulsion phase. The point of introduction of heavy phase through line 90 should be sufficiently above the point of introduction of the light phase to allow for sufficient mixing of the two phases in the mixing section resulting in the extraction of phosphorus-containing ligands into the light phase. The intimate mixing of light and heavy phase in mixing section 72 may be promoted by mechanical or static mixing apparatus not shown in FIG. 3. For example, mixing section 72 may comprise packing, baffles or perforated plates, not shown in FIG. 3.

The heavy phase 82 settles into collection section 74 and passes out of the column 70 through line 96. Light phase 86 settles in collection section 76 and passes from the column through line 92.

Figure 4:
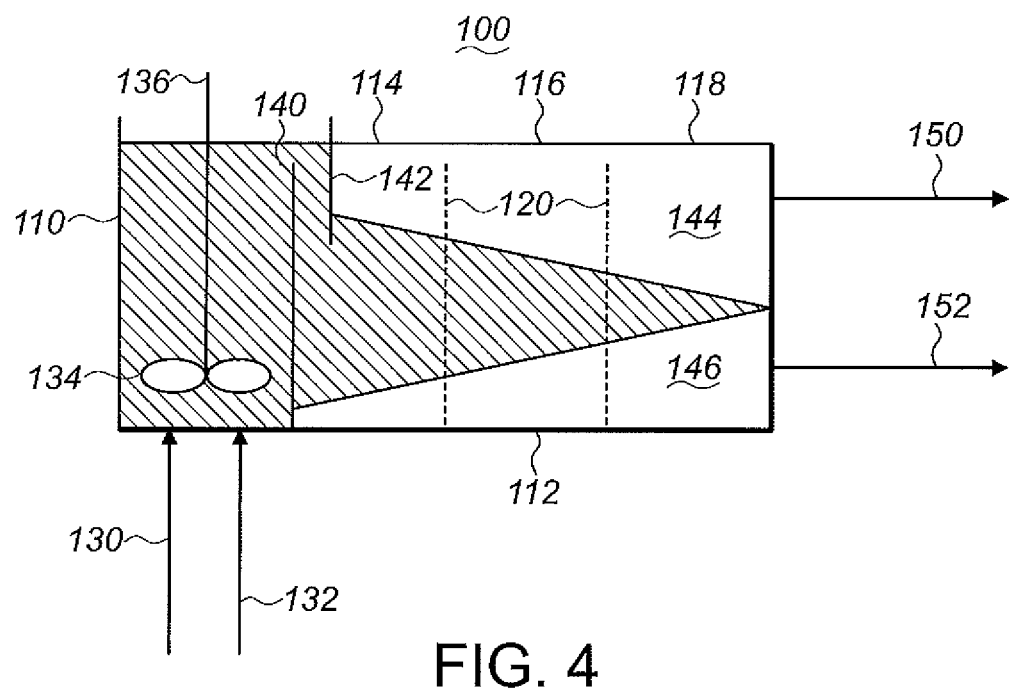
FIG. 4 is a diagram showing a mixing/settling apparatus having three chambers in the settling section.

FIG. 4 provides a representation of a mixer-settler 100 having a multistage settling section. Mixer-settler 100 has a mixing section 110 and a settling section 112. In mixer-settler 100, the mixing section 110 is separate from the settling section 112. The settling section has three compartments, represented in FIG. 4 as sections 114, 116, and 118. These sections are separated by coalescence plates 120. The coalescence plates 120 may be designed to provide flow of separated light and heavy phases between chambers, while restricting the flow of emulsion phase between chambers. A feed comprising a phosphorus-containing ligand is passed into the mixing section 110 via line 130. The extraction solvent is introduced into mixing section 110 via line 132. The mixing section 110 includes an impeller 134 mounted on shaft 136 to provide for mechanical mixing of fluids. Mixing of the feeds provides a mixed phase comprising an emulsion phase represented in FIG. 4 by shading 140.

The mixed phase 140 flows into the settling section 112 as an overflow from the mixing section 110. This mixed phase 140 is prevented from flowing directly into the light phase 144 by baffle plate 142. As settling occurs in settling section 112, the volume of the mixed phase 140 decreases, the volume of the light phase 144 increases, and the volume of the heavy phase 146 increases. Heavy phase 146 is removed from settling section 112, in particular from chamber 118, via line 152 and light phase 144 is removed from settling section 112, in particular, from chamber 118, via line 150.

It is desirable for both a mononitrile and a dinitrile to be present in the countercurrent contactor. For a discussion of the role of monodentate and bidentate ligand in extraction of hydrocyanation reactor effluent streams, see U.S. Pat. No. 3,773,809 to Walter and U.S. Pat. No. 6,936,171 to Jackson and McKinney.

For the process disclosed herein, suitable molar ratios of mononitrile to dinitrile components include 0.01 to 2.5, for example, 0.1 to 1.5, for example, 0.1 to 0.65, for example 0.10 to 0.30.

Maximum temperature is limited by the volatility of the hydrocarbon solvent utilized, but recovery generally improves as the temperature is increased. Examples of suitable operating ranges are 20° C. to 100° C., 20° C. to 80° C., 40° C. to 80° C., and 40° C. to 70° C.

The controlled addition of monophosphite ligands may enhance settling. Examples of monophosphite ligands that may be useful as additives include those disclosed in Drinkard et al U.S. Pat. No. 3,496,215, U.S. Pat. No. 3,496,217, U.S. Pat. No. 3,496,218, U.S. Pat. No. 5,543,536, and published PCT Application WO 01/36429 (BASF).

As described herein, the addition of polyamine from step (vi) to a mixture comprising phosphorus-containing ligand, organic mononitriles and organic dinitriles enhances settling, especially when the mixture comprises a Lewis acid, such as $ZnCl_2$. Polyamines are organic compounds having two or more amino groups. The addition of polyamine tends to reduce or eliminate any inhibiting effect of Lewis acid on catalyst and ligand recovery.

The reaction product of Lewis acid with polyamine may become entrained in a raffinate phase as it moves through a multistage countercurrent liquid-liquid extractor. In particular, this product may form a precipitate in the raffinate phase in the form of a complex of Lewis acid with polyamine. It will be understood that the polyamine is a Lewis base. This precipitate may exist as a dispersion of fine particles distributed throughout the raffinate phase. This precipitate may be removed by conventional techniques, such as filtration or centrifugation, after the raffinate is removed from the last stage (i.e. the second terminal mixer-settler) of the multistage countercurrent liquid-liquid extractor.

The extracted phosphorus-containing ligands comprise free ligands (e.g., those which are not complexed to nickel) and those which are complexed to nickel. Accordingly, it will be understood that extraction processes described herein are useful for recovering phosphorus-containing ligands which are included in metal/ligand complexes, such as a complex of zero valent nickel with at least one ligand comprising a bidentate-phosphorus containing ligand.

Hydrocyanation of 3PN to Make ADN

Processes for reacting 3-pentenenitrile (3PN) with HCN to make adiponitrile (ADN) are well known. Examples of such processes are described, for example, in International Published Patent Application WO 2012005917 and United States Patent Application Publication No. 2013/0211126.

3PN hydrocyanation may be performed by reacting HC≡N and 3PN as a vapor, liquid, or mixtures thereof.

In the 3PN hydrocyanation reaction, promoters are provided to enhance the production of dinitriles. As known in the art, promoters influence both catalyst activity and selectivity to the desired ADN. Promoters employed include salts of metals having atomic numbers 13, 21-32, 39-50, and 57-80, for example, zinc, and compounds of the formula $BR'_3$ wherein R' is an alkyl or an aryl radical of up to 18 carbon atoms, for example triphenylboron, $(C_6H_5)_3B$. The anions of the metal salts include halides, for example chloride, sulfates, phosphates, and lower aliphatic carboxylates. Useful promoters are generally known in the art as Lewis acids. The mole ratio of promoter to nickel in the catalyst is sufficient to promote the hydrocyanation of 3-pentenenitrile, and in one embodiment may be in the range of 0.6:1 to 1.2:1, for example, from 0.9:1 to 1.1:1 when the Lewis acid promoter is $ZnCl_2$.

The 3PN hydrocyanation reaction temperature may be maintained within the range of about 0° C. to about 150° C., for example, within the range of about 25° C. to about 80° C. Generally, the reaction pressure should be sufficient to maintain the HC≡N in contact with the catalyst dissolved in the liquid reaction mixture. Such pressure is at least, in part, a function of the amount of unreacted HC≡N present in the reaction mixture. While an upper limit of pressure for this reaction step is not limited to any particular pressure, for practical purposes the pressure generally ranges from about 15 psia to about 45 psia (about 1.0 bar to about 3.0 bar).

The overall feed molar ratio of 3PN to HC≡N may be in the range of 1:1 to 2.0:1, for example, in the range of 1:1 to about 1.2:1.

The molar ratio of HC≡N to catalyst in the reaction of 3PN with HC≡N may be in the range of 200:1 to 2500:1, for example, 500:1 to 1250:1, for example, in the range 500:1 to 1000:1.

The phosphorus-containing ligand used in the reaction of 3PN with HC≡N is, preferably, a bidentate ligand. The molar ratio of bidentate ligand to nickel in the catalyst for the 3PN hydrocyanation step may be from 1:1 to 5:1, for example, 1:1 to 3:1, for example, 1:1 to 1.5:1.

The residence time in the 3PN hydrocyanation reaction zone for this reaction step is typically determined by the desire to obtain a certain degree of conversion of penteneni-triles, HC≡N, or a combination thereof. In addition to residence time, catalyst concentration and reaction temperature will also affect conversion of reactants to products. Generally, residence times will be in the range of about 5 hour to about 40 hours, for example, in the range of about 15 hour to about 30 hours. The HC≡N conversion may be greater than 99%.

The HC≡N feed, the 3PN-containing feed, and the catalyst composition are contacted in a reaction zone which may be contained in any suitable equipment known to one skilled in the art. One or more pieces of conventional equipment may be used to provide the reaction zone, for example continuous stirred-tank reactors and loop-type reactors, or combinations thereof, optionally with apparatus for removing at least a portion of the heat of reaction.

Diphosphite Ligands

Examples of bidentate phosphite ligands useful in the invention include those having the following structural formulae:

(R$^1$O)$_2$P(OZO)P(OR$^f$)$_2$,     I

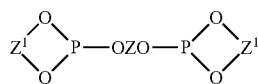

II

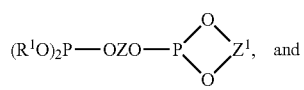

(R$^1$O)$_2$P—OZO—P⟨⟩Z$^1$, and     III wherein in I, II and III, R$^1$ is phenyl, unsubstituted or substituted with one or more C$_1$ to C$_{12}$ alkyl or C$_1$ to C$_{12}$ alkoxy groups; or naphthyl, unsubstituted or substituted with one or more C$_1$ to C$_{12}$ alkyl or C$_1$ to C$_{12}$ alkoxy groups; and Z and Z$^1$ are independently selected from the group consisting of structural formulae IV, V, VI, VII, and VIII:

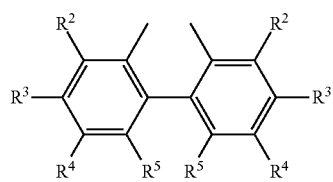

IV

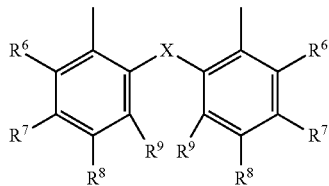

V and wherein
R$^2$, R$^3$, R$^4$, R$^5$, R$^6$, R$^1$, R$^8$, and R$^9$ are independently selected from the group consisting of H, C$_1$ to C$_{12}$ alkyl, and C$_1$ to C$_{12}$ alkoxy;
X is O, S, or CH(R$^{10}$);
R$^{10}$ is H or C$_1$ to C$_{12}$ alkyl;

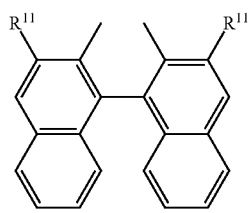

VI

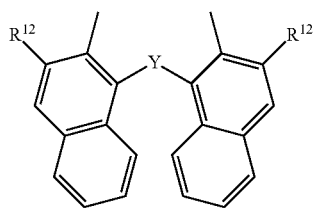

VII and wherein
R$^{11}$ and R$^{12}$ are independently selected from the group consisting of H, C$_1$ to C$_{12}$ alkyl, and C$_1$ to C$_{12}$ alkoxy; and CO$_2$R$^{13}$;
R$^{13}$ is C$_1$ to C$_{12}$ alkyl or C$_6$ to C$_{10}$ aryl, unsubstituted or substituted. with C$_1$ to C$_4$ alkyl;
Y is O, S, or CH(R$^{14}$);
R$^{14}$ is H or C$_1$ to C$_{12}$ alkyl;

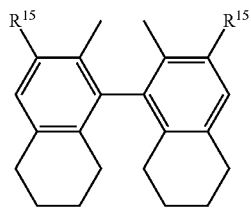

VIII wherein
R$^{15}$ is selected from the group consisting of H, C$_1$ to C$_{12}$ alkyl, and C$_1$ to C$_{12}$ alkoxy and CO$_2$R$^{16}$;
R$^{16}$ is C$_1$ to C$_{12}$ alkyl or C$_6$ to C$_{10}$ aryl, unsubstituted or substituted with C$_1$ to C$_4$ alkyl.

In the structural formulae I through VIII, the C$_1$ to C$_{12}$ alkyl, and C$_1$ to C$_{12}$ alkoxy groups may be straight chain or branched.

A particular example of a formula of a bidentate phosphite ligand that is useful in the present process is that having the Formula X, shown below

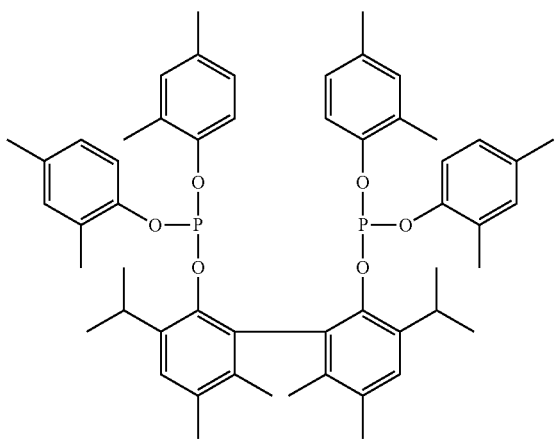

Other examples of bidentate phosphite ligands are those having the formula XX, shown below

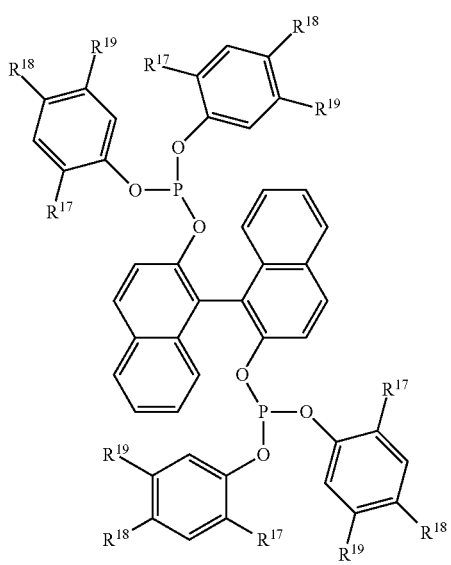

where $R^{17}$ is selected from the group consisting of methyl, ethyl or isopropyl, and $R'^{8}$ and $R^{19}$ are independently selected from H or methyl.

Further examples of bidentate phosphite ligands are described in WO 2013/053610.

Additional suitable bidentate phosphites are of the type disclosed in U.S. Pat. Nos. 5,512,695; 5,512,696; 5,523,453; 5,663,369; 5,693,843; 5,688,986; 5,723,641; 5,847,101; 5,959,135; 6,120,700; 6,171,996; 6,171,997; 6,399,534.

Diphosphonite Ligands

The diphosphonite-containing ligand may be a diphosphonite ligand of formula (L):

$(R^1)(R^2—O)P—O—Y—O—P(O—R^3)(R^4)$     L where $R^1$ and $R^2$ are each independently identical or different, separate or bridged organic radicals; $R^3$ and $R^4$ are each independently identical or different, separate or bridged organic radicals; and Y is a bridging group.

The $R^1$ and $R^2$ radicals may each independently be identical or different organic radicals. Examples of $R^1$ and $R^2$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^3$ and $R^4$ radicals may each independently be identical or different organic radicals. Examples of $R^3$ and $R^4$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^1$ and $R^2$ radicals may each be separate or bridged. The $R^3$ and $R^4$ radicals may also each be separate or bridged. The $R^1$, $R^2$, $R^3$ and $R^4$ radicals may each be separate, two may be bridged and two separate, or all four may be bridged.

Examples of phosphonite-containing ligands of formula (L) may be diphosphonite ligands of formula (LI) or (formula LII):

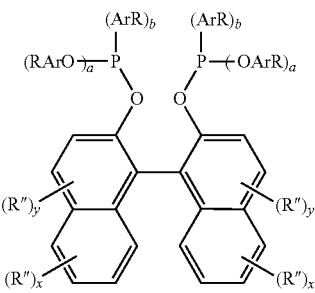

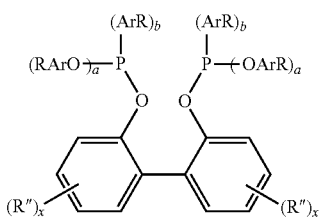

wherein:

x=0 to 4;

y=0 to 2;

a and b are, in one embodiment, individually 0, 1, or 2, provided a+b=2, and in another embodiment, are both equal to 1;

each Ar is individually phenyl or naphthyl, and the two Ar groups that are directly or indirectly (through an oxygen) bonded to the same phosphorus atom may be linked to each other by a linking unit selected from the group consisting of direct bond, alkylidene, secondary or tertiary amine, oxygen, sulfide, sulfone, and sulfoxide;

each R is individually hydrogen, ethenyl, propenyl, acryloyl, methacryloyl, an organic radical with a terminal ethenyl, propenyl, acryloyl, or methacryloyl group, linear or branched alkyl, cycloalkyl, acetal, ketal, aryl, alkoxy, cycloalkoxy, aryloxy, formyl, ester, fluorine, chlorine, bromine, perhaloalkyl, hydrocarbylsulfinyl, hydrocarbylsulfonyl, hydrocarbylcarbonyl or cyclic ether;

each Ar can be further substituted with linear or branched alkyl, cycloalkyl, acetal, ketal, aryl, alkoxy, cycloalkoxy, aryloxy, formyl, ester, fluorine, chlorine, bromine, perhaloalkyl, hydrocarbylsulfinyl, hydrocarbylsulfonyl, hydrocarbylcarbonyl or cyclic ether;

each R" is individually hydrogen, ethenyl, propenyl, an organic radical with a terminal ethenyl or propenyl group, linear or branched alkyl, cycloalkyl, acetal, ketal, aryl, alkoxy, cycloalkoxy, aryloxy, formyl, ester, fluorine, chlorine, bromine, perhaloalkyl, hydrocarbylsulfinyl, hydrocarbylsulfonyl, hydrocarbylcarbonyl or cyclic ether.

At least one R in formula (LI) or formula (LII) may represent ethenyl, propenyl, acryloyl, methacryloyl or the organic radical with a terminal ethenyl, propenyl, acryloyl, or methacryloyl group and/or at least one R" may represent ethenyl, propenyl, or the organic radical with a terminal ethenyl or propenyl group.

Examples of diphosphonite ligands of formula (LII) are compounds of formula (LIII) and formula (LIV):

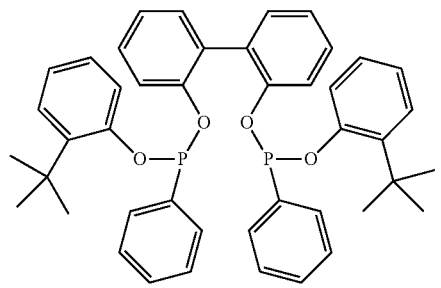

LIII

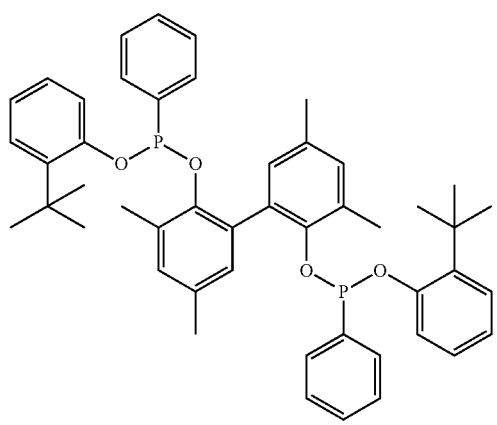

LIV

Diphosphonite ligands and the synthesis of these diphosphonite ligands are described in U.S. Pat. No. 6,924,345 and in U.S. Pat. No. 7,935,229.

Extraction Solvent

Suitable hydrocarbon extraction solvents include paraffins and cycloparaffins (aliphatic and alicyclic hydrocarbons) having a boiling point in the range of about 30° C. to about 135° C., including n-pentane, n-hexane, n-heptane and n-octane, as well as the corresponding branched chain paraffinic hydrocarbons having a boiling point within the range specified. Useful alicyclic hydrocarbons include cyclopentane, cyclohexane and cycloheptane, as well as alkyl substituted alicyclic hydrocarbons having a boiling point within the specified range. Mixtures of hydrocarbons may also be used, such as, for example, mixtures of the hydrocarbons noted above or commercial heptane which contains a number of hydrocarbons in addition to n-heptane. Cyclohexane is the preferred extraction solvent.

Recovery of Adiponitrile

The lighter (hydrocarbon) phase recovered from the multistage countercurrent liquid-liquid extractor is directed to suitable equipment to recover catalyst, reactants, etc. for recycle to the hydrocyanation, while the heavier (lower) phase containing dinitriles recovered from the multistage countercurrent liquid-liquid extractor is directed to product recovery after removal of any solids, which may accumulate in the heavier phase. These solids may contain valuable components which may also be recovered, e.g., by the process set forth in U.S. Pat. No. 4,082,811.

The solids in the heavier phase, also referred to herein as the raffinate phase, may comprise a complex of Lewis acid and polyamine in the form of dispersion of fine particles. The raffinate phase may also comprise extraction solvent, such as cyclohexane, pentenenitriles, which comprise 3-pentenenitrile, compounds with a higher boiling point than adiponitrile and compounds with a boiling point greater than the boiling point of pentenenitriles and less than the boiling point of adiponitrile. The complex of Lewis acid and polyamine may be removed from the raffinate phase prior to removing extraction solvent, and especially before removing pentenenitriles from the raffinate phase.

The complex of Lewis acid and polyamine may be formed, at least in part, prior to extraction step (iv), and removed at least in part, prior to extraction step (iv).

The complex of Lewis acid and polyamine may be removed by any customary solids removal process. Examples of such processes include filtration, crossflow filtration, centrifugation, sedimentation, classification and decantation. Common apparatus for such solids removal include filters, centrifuges and decanters.

It has been found that the complex of Lewis acid and polyamine may catalyze the unwanted cyclization reaction of adiponitrile to form 2-cyanocyclopentylideneimine (CPI), especially when the raffinate phase is heated to temperatures used in the column, discussed hereinafter, which is used to separate dinitriles, which comprise adiponitrile, from compounds having a boiling point higher than adiponitrile.

Figure 5:
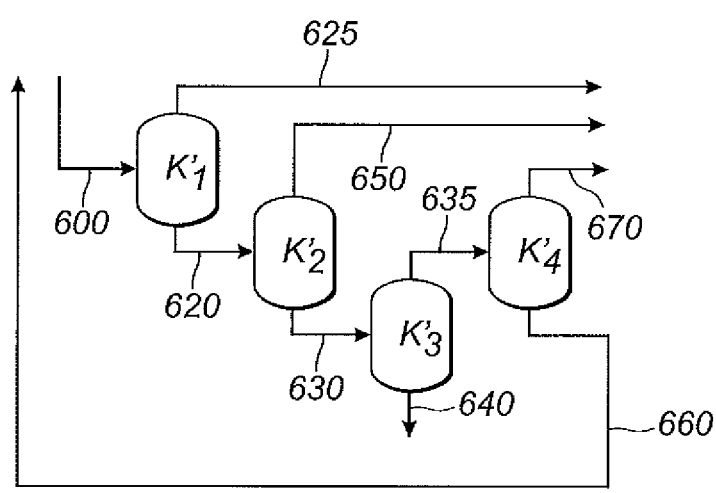
FIG. 5 is a diagram showing a distillation train which may be used to recover adiponitrile from a raffinate stream.

FIG. 5 shows a distillation train, which may be used as an adiponitrile purification section. FIG. 5 of the present application corresponds to FIG. 3 of United States Patent Application Publication No. 2013/0211126. Line 600 transports a raffinate stream from an extraction zone into distillation column $K'_1$, where extraction solvent is separated from higher boiling components of the raffinate stream. In particular, extraction solvent, such as cyclohexane, is withdrawn from distillation column $K'_1$ through line 625, and higher boiling components of the raffinate stream are withdrawn from distillation column $K'_1$ through line 620.

The solvent-depleted stream in line 620 is then passed into distillation column $K'_2$, where pentenenitrile is separated from higher boiling components remaining in the raffinate stream. In particular, pentenenitrile, such as 3PN and any 2M3BN present, is withdrawn from distillation column $K'_2$ through line 650, and higher boiling components of the raffinate stream are withdrawn from distillation column $K'_2$ through line 630.

The pentenenitrile-depleted stream in line 630 is then passed into distillation column $K'_3$, where dinitriles are separated from higher boiling components remaining in the raffinate stream. In particular, dinitriles, such as ADN and MGN, are withdrawn from distillation column $K'_3$ through line 635, and higher boiling components of the raffinate stream are withdrawn from distillation column $K'_3$ through line 640. These higher boiling components in line 640 may comprise, for example, catalyst degradation products.

The dinitrile-enriched stream in line 635 is then passed into distillation column K'$_4$, where adiponitrile is separated from lower boiling dinitriles, such as MGN. In particular, MGN is withdrawn from distillation column K'$_4$ through line 670, and a purified adiponitrile stream is withdrawn from distillation column K'$_4$ through line 660.

Although not shown in FIG. 5, a complex of Lewis acid and Lewis base in the form of a dispersed solid precipitate may be removed, e.g., by filtration, from the raffinate before the stream is introduced into distillation column K'$_1$. According to another embodiment, this complex may be removed from the stream in line 620 before this stream enters distillation column K'$_2$. According to another embodiment, this complex may be removed from the stream in line 630 before this stream enters distillation column K'$_3$.

Production of Hexamethylene Diamine (HMD)

Hexamethylene diamine (HMD) may be produced by feeding hydrogen and adiponitrile (ADN) into hydrogenation reaction zone containing a suitable hydrogenation catalyst, while maintaining the reaction zone under reaction conditions to convert ADN and hydrogen into HMD. Hydrogenation reactions for converting ADN and hydrogen into HMD are described in U.S. Pat. No. 3,696,153, U.S. Pat. No. 3,758,584 and U.S. Pat. No. 5,105,015.

A diluent may be cofed to the hydrogenation reaction zone along with ADN and hydrogen (H$_2$). The hydrogenation reaction of ADN with hydrogen is exothermic. The diluent may act as a heat sink to provide better control of temperatures in the reaction zone. An example of a suitable diluent is ammonia (NH$_3$).

The hydrogenation catalyst may comprise Group VIII elements including iron, cobalt, nickel, rhodium, palladium, ruthenium and combinations thereof. The catalyst may also contain one or more promoters in addition to the Group VIII elements mentioned above, for example, one or more Group VIB elements such as chromium, molybdenum, and tungsten. The promoters may be present in concentrations 0.01 to 15 percent based on the weight of the catalyst, for example, from 0.5 to 5 percent. The hydrogenation catalyst may also be in the form of an alloy, including a solid solution of two or more metals, or an individual metal or a sponge metal catalyst. A "sponge metal" is one, which has an extended porous "skeleton" or "sponge-like" structure, preferably a base metal (e.g. iron, cobalt or nickel), with dissolved aluminum, optionally containing promoter(s). The amount of iron, cobalt or nickel present in the hydrogenation catalyst may vary. Skeletal catalysts useful as hydrogenation catalyst may contain iron, cobalt or nickel in an amount totaling from about 30 to about 97 weight % iron, cobalt and/or nickel, for example, from about 85 to about 97 weight % iron, cobalt or nickel, for example, 85-95% nickel. Sponge catalysts may be modified with at least one metal, for example, selected from the group consisting of chromium and molybdenum. The sponge metal catalysts may also contain surface hydrous oxides, adsorbed hydrogen radicals, and hydrogen bubbles in the pores. The hydrogenation catalyst may also include aluminum, for example, from about 0.2 to 3.0 weight % aluminum, for example from about 0.5 to 1.5 weight % aluminum. Commercially available hydrogenation catalysts of the sponge type are promoted or unpromoted Raney® Ni or Raney® Co catalysts that can be obtained from the Grace Chemical Co. (Columbia, Md.). Catalysts comprising Group VIII metals are described in U.S. Pat. No. 6,376,714.

The hydrogenation catalyst may be supported or unsupported.

A hydrogenation catalyst may be prepared by reducing an oxide of a Group VIII metal with hydrogen. For example, a hydrogenation catalyst may be activated by reducing at least a part of iron oxide to metallic iron by heating it in the presence of hydrogen at a temperature above 200° C. but not above 600° C. Activation may be continued until at least 80% by weight of the available oxygen in the iron has been removed and may be continued until substantially all, for example, from 90 to 98% of the available oxygen has been removed. During the activation it is desirable to prevent back-diffusion of water-vapor formed. Examples of catalyst activation techniques are described in U.S. Pat. No. 3,986,985.

The hydrogenation reaction may take place at under a wide range of pressures, for example, from 50 to 6,000 psi. Raney® cobalt or nickel catalyst may be used in low pressure hydrogenation reactions, which take place, for example at pressures from 250 to 750 psi. Reduced iron oxide catalysts may be used in high pressure hydrogenation reactions, which take place, for example at pressures from 4,000 to 6,000 psi. When ammonia is used as a diluent in a high pressure hydrogenation reaction, the ammonia may be in a liquid or super critical fluid state.

The temperature in the hydrogen reaction zone may be, for example, from 50 to 200° C., for example, from 80 to 165° C.

The hydrogenation reaction may take place in a continuous or batch manner. The hydrogenation catalyst in the hydrogenation reaction zone may be in a fixed bed or a slurry reactor.

The hexamethylene diamine (HMD) product and byproducts, such as bis-hexamethylene triamine (BHMT) and 1,2-diaminocyclohexane may be separated from one another by conventional distillation techniques.

EXAMPLES

Examples 1-6 describe representative embodiments of processes for making adiponitrile. Example 7-45 provide comparative data regarding the ability of hexamethylene diamine (HMD), bis-hexamethylene triamine (BHMT) and 1,2-diaminocyclohexane (DCH) to promote a separation step in a process for making adiponitrile. Examples 46-53 demonstrate the ability of a complexes of ZnCl$_2$ with BHMT or HMD to catalyze the cyclization of adiponitrile (ADN) to 2-cyanocyclopentylideneimine (CPI) under conditions encountered when a raffinate stream is refined to produce purified ADN. Comparative Examples are, on occasion, also referred to as "Examples" herein.

Example 1

This Example describes a process for making adiponitrile. A step of this process involves the use of a catalyst with a diphosphite ligand.

3-Pentenenitrile (3-PN), hydrogen cyanide (HCN), zero valent nickel, a diphosphite-containing compound and a Lewis acid are introduced into a hydrocyanation reaction zone. The hydrocyanation reaction zone is maintained under conditions sufficient to convert 3-PN and HCN to adiponitrile (ADN). The Lewis acid is ZnCl$_2$. The diphosphite ligand is a compound having the Formula X, shown below.

X

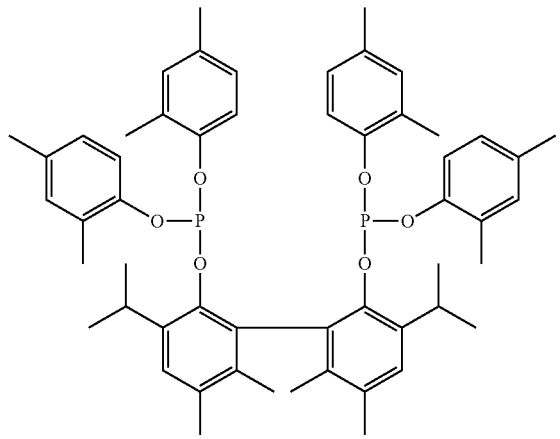

LIV

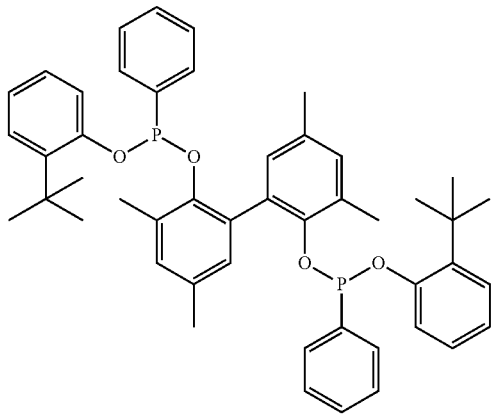

A product stream is withdrawn from the hydrocyanation reaction zone. The product stream comprises 3-PN, ADN, zero valent nickel, the diphosphite-containing compound and a Lewis acid. The composition of the product stream is approximately:

85% by weight $C_6$ dinitriles
14% by weight $C_5$ mononitriles
1% by weight catalyst components
200 ppm by weight active nickel
230 ppm by weight zinc.

The product stream is contacted with an extraction solvent under conditions to obtain a two phase mixture comprising a light phase and a heavy phase. The light phase comprises extraction solvent and the diphosphite-containing compound. The heavy phase comprises 3-PN and ADN.

ADN is recovered from the heavy phase. ADN recovered from the heavy phase is reacted with hydrogen to produce hexamethylene diamine (HMD) as a product amine. Bis-hexamethylene triamine (BHMT) and 1,2-diaminocyclohexane (DCH) are also produced as byproduct amines.

Hexamethylene diamine (HMD) produced by reacting ADN with hydrogen is then contacted with the product stream withdrawn from the hydrocyanation reaction zone.

Example 2

Example 1 is repeated except that bis-hexamethylene triamine (BHMT), instead of hexamethylene diamine (HMD), produced by reacting ADN with hydrogen is contacted with the product stream withdrawn from the hydrocyanation reaction zone.

Example 3

Example 1 is repeated except that 1,2-diaminocyclohexane, instead of hexamethylene diamine (HMD), produced by reacting ADN with hydrogen is contacted with the product stream withdrawn from the hydrocyanation reaction zone.

Example 4

Example 1 is repeated except that a diphosphonite-containing ligand is substituted for the diphosphite-containing ligand. The diphosphonite-containing ligand is a compound having the Formula LIV, shown below.

Example 5

Example 4 is repeated except that bis-hexamethylene triamine (BHMT), instead of hexamethylene diamine (HMD), produced by reacting ADN with hydrogen is contacted with the product stream withdrawn from the hydrocyanation reaction zone.

Example 6

Example 4 is repeated except that 1,2-diaminocyclohexane (DCH), instead of hexamethylene diamine (HMD), produced by reacting ADN with hydrogen is contacted with the product stream withdrawn from the hydrocyanation reaction zone.

In the following Examples, values for extraction coefficient are the ratio of weight fraction of catalyst in the extract phase (hydrocarbon phase) to the weight fraction of catalyst in the raffinate phase (organonitrile phase). An increase in extraction coefficient results in greater efficiency in recovering catalyst. As used herein, the terms, light phase, extract phase and hydrocarbon phase, are synonymous. Also, as used herein, the terms, heavy phase, organonitrile phase and raffinate phase, are synonymous.

Analyses of the extract and the raffinate streams of the catalyst extraction were conducted on an Agilent 1100 series HPLC and via ICP. The HPLC was used to determine the extraction efficiency of the process.

In the Examples which follow, a diphosphite ligand is present. However, it is believed that the results of these Examples would be essentially the same if a different phosphorus-containing ligand, such as a diphosphonite ligand, was substituted for the diphosphite ligand.

Comparative Example 7

To a 50 mL, jacketed, glass laboratory extractor, equipped with a magnetic stirbar, digital stir-plate, and maintained at 65° C., was charged 10 grams of the product of a pentenenitrile-hydrocyanation reaction, and 10 grams of the extract from the second stage of a mixer-settler cascade, operated in counter-current flow. This extract from the second stage comprised approximately 50 ppm nickel and 3100 ppm diphosphite ligand. The hexamethylene diamine concentration in the system was 0 ppm.

The reactor product was approximately:
85% by weight $C_6$ dinitriles
14% by weight $C_5$ mononitriles
1% by weight catalyst components
200 ppm by weight active nickel
230 ppm by weight zinc.

The laboratory reactor was then mixed at 500 rotations-per-minute, for 10 minutes, and then allowed to settle for 1 minute. After settling for 1 minute, a stable emulsion was present throughout the extract phase. Samples were obtained of the extract and raffinate phases of the extractor after settling and analyzed to determine the extent of catalyst extraction. The ratio of active nickel present in the extract phase vs. the raffinate phase was found to be 5. The concentration of zinc in the raffinate was found to be 230 ppm.

Example 8

Comparative Example 7 was repeated except that hexamethylene diamine (HMD) was added to the system. In particular, a sufficient amount of HMD was added so that the molar ratio of Zn/HMD was 12 in the system.

Example 9

Comparative Example 7 was repeated except that hexamethylene diamine (HMD) was added to the system. In particular, a sufficient amount of HMD was added so that the molar ratio of Zn/HMD was 6 in the system.

Example 10

Comparative Example 7 was repeated except that hexamethylene diamine (HMD) was added to the system. In particular, a sufficient amount of HMD was added so that the molar ratio of Zn/HMD was 2.4 in the system.

Example 11

Comparative Example 7 was repeated except that hexamethylene diamine (HMD) was added to the system. In particular, a sufficient amount of HMD was added so that the molar ratio of Zn/HMD was 1.2 in the system.

Example 12

Comparative Example 7 was repeated except that bis-hexamethylene triamine (BHMT) was added to the system. In particular, a sufficient amount of BHMT was added so that the molar ratio of Zn/BMHT was 5.9 in the system.

Example 13

Comparative Example 7 was repeated except that bis-hexamethylene triamine (BHMT) was added to the system. In particular, a sufficient amount of BHMT was added so that the molar ratio of Zn/BMHT was 2.9 in the system.

Example 14

Comparative Example 7 was repeated except that bis-hexamethylene triamine (BHMT) was added to the system. In particular, a sufficient amount of BHMT was added so that the molar ratio of Zn/BMHT was 1.2 in the system.

Example 15

Comparative Example 7 was repeated except that bis-hexamethylene triamine (BHMT) was added to the system. In particular, a sufficient amount of BHMT was added so that the molar ratio of Zn/BMHT was 12 in the system.

Example 16

Comparative Example 7 was repeated except that 1,2-diaminocyclohexane (DCH) was added to the system. In particular, a sufficient amount of DCH was added so that the molar ratio of Zn/DCH was 1.6 in the system.

Example 17

Comparative Example 7 was repeated except that 1,2-diaminocyclohexane (DCH) was added to the system. In particular, a sufficient amount of DCH was added so that the molar ratio of Zn/DCH was 2 in the system.

Example 18

Comparative Example 7 was repeated except that 1,2-diaminocyclohexane (DCH) was added to the system. In particular, a sufficient amount of DCH was added so that the molar ratio of Zn/DCH was 4 in the system.

Example 19

Comparative Example 7 was repeated except that 1,2-diaminocyclohexane (DCH) was added to the system. In particular, a sufficient amount of DCH was added so that the molar ratio of Zn/DCH was 8 in the system.

Example 20

Comparative Example 7 was repeated except that triethylamine (TEA) was added to the system. In particular, a sufficient amount of TEA was added so that the molar ratio of Zn/TEA was 1 in the system.

Example 21

Comparative Example 7 was repeated except that octylamine was added to the system. In particular, a sufficient amount of octylamine was added so that the molar ratio of Zn/octylamine was 1.3 in the system.

Comparative Example 22

Comparative Example 7 was repeated except that polyethyleneglycol (PEG-600) was added to the system. In particular, a sufficient amount of PEG-600 was added so that the molar ratio of Zn/PEG-600 was 1.5 in the system.

Comparative Example 23

Comparative Example 7 was repeated except that adipamide was added to the system. In particular, a sufficient amount of adipamide was added so that the molar ratio of Zn/adipamide was 2.3 in the system.

Comparative Example 24

Comparative Example 7 was repeated except that triphenyl phosphine ($Ph_3P$) was added to the system. In particular, a sufficient amount of $Ph_3P$ was added so that the molar ratio of Zn/$Ph_3P$ was 1 in the system.

Example 25

Comparative Example 7 was repeated except that calcium hydroxide (Ca(OH)$_2$) was added to the system. In particular, a sufficient amount of Ca(OH)$_2$ was added so that the molar ratio of Zn/Ca(OH)$_2$ was 0.3 in the system.

Results of Examples 7-25 are summarized in Table 1.

TABLE 1

| Ex./CEx. | Temp (° C.) | Time (min) | Zn/Additive | Additive | KLL | Zn/Ni |
|---|---|---|---|---|---|---|
| 7 | 65 | 10 | | None | 5 | 1.15 |
| 8 | 65 | 10 | 12.0 | HMD | 13 | 1.09 |
| 9 | 65 | 10 | 6.0 | HMD | 13 | 1.11 |
| 10 | 65 | 10 | 2.4 | HMD | 23 | 0.43 |
| 11 | 65 | 10 | 1.2 | HMD | 84 | 0.12 |
| 12 | 65 | 10 | 5.9 | BHMT | 102 | 0.12 |
| 13 | 65 | 10 | 2.9 | BHMT | 80 | 0.17 |
| 14 | 65 | 10 | 1.2 | BHMT | 112 | 0.17 |
| 15 | 65 | 10 | 12.0 | BHMT | 18 | |
| 16 | 65 | 10 | 1.6 | DCH | 119 | 0.85 |
| 17 | 65 | 10 | 2 | DCH | 114 | |
| 18 | 65 | 10 | 4 | DCH | 27 | 1.03 |
| 19 | 65 | 10 | 8 | DCH | 8 | 1.05 |
| 20 | 65 | 10 | 1 | TEA | 20 | 0.94 |
| 21 | 65 | 10 | 1.3 | Octylamine | 63 | 0.96 |
| 22 | 65 | 10 | 1.5 | PEG-600 | 5 | 1.07 |
| 23 | 65 | 10 | 2.3 | Adipamide | 6 | |
| 24 | 65 | 10 | 1 | Ph$_3$P | 4 | 1.15 |
| 25 | 65 | 10 | 0.3 | Ca(OH)$_2$ | 14 | |

KLL = amount of catalyst in the extract/amount of catalyst in the raffinate;
Zn/Additive = the molar ratio of the zinc-to-additive during extraction;
Zn/Ni = the ratio of the total amount of zinc-to-nickel remaining in both phases after the extraction, as determined by inductively coupled plasma spectrometry (ICP).

The data summarized in Table 1 represent evaluations of a number of materials as potential additives for improved catalyst extraction. Examples 7-11 show the beneficial effect of hexamethylene diamine (HMD) on catalyst extraction, as the HMD loading increases (represented by decreasing Zn/Additive ratio) the catalyst extraction efficiency (represented by KLL) increases. Examples 12-15 show the beneficial effect of bis-hexamethylene triamine (BHMT) on catalyst extraction. Examples 16-19 show the beneficial effect of 1,2-diaminocyclohexane (DCH) on catalyst extraction. Example 20 shows the effect of adding octylamine on catalyst extraction. Example 25 shows the effect of calcium hydroxide on catalyst extraction. By way of contrast, Comparative Examples 22-24 show little effect on catalyst extraction using PEG-600, adipamide, and triphenyl phosphine, respectively.

The results in Table 1 show that BHMT produced superior results. For example, as compared with HMD, at a Zn/Additive ratio of 1.2, BHMT produced a greater KLL value than HMD. As compared with DCH, BHMT produced a greater KLL value and a smaller Zn/Ni ratio, when used at a Zn/Additive ratio of 5.9, than DCH, when used at a Zn/Additive ratio of 4. As compared with octylamine, BHMT produced a greater KLL value and a smaller Zn/Ni ratio, when used at a Zn/Additive ratio of 1.2, than octylamine, when used at a Zn/Additive ratio of 1.3.

Examples 26 and 27

These Examples demonstrate the effect of adding hexamethylene diamine (HMD) to the extraction zone.

Comparative Example 7 was repeated except that hexamethylene diamine was added to the product of a pentene-hydrocyanation reaction. To a 50 mL, jacketed, glass laboratory extractor, equipped with a magnetic stirbar, digital stir-plate, and maintained at 65° C., was charged 10 grams of the product of pentenenitrile-hydrocyanation reactor product, and 10 grams of the extract from the second stage of a mixer-settler cascade, operated in counter-current flow.

The reactor product was approximately:
85% by weight C$_6$ dinitriles
14% by weight C$_5$ mononitriles
1% by weight catalyst components
360 ppm by weight active nickel.

The laboratory reactor was then mixed at 1160 rotations-per-minute, for 20 minutes, and then allowed to settle for 15 minutes. A stable emulsion was present throughout the extract phase in the absence of the addition of HMD. After 15 minutes of settling, essentially no emulsion phase was present when HMD was added. Samples were obtained of the extract and raffinate phases of the extractor and analyzed to determine the extent of catalyst extraction.

TABLE 5

Effect of hexamethylene diamine on catalyst extraction

| Example | Concentration of HMD added (ppm) | Catalyst recovery (KLL) | Stable emulsion |
|---|---|---|---|
| 7 | 0 | 14 | Yes |
| 26 | 250 | 43 | No |
| 27 | 500 | 80 | No |

Comparative Examples 28-30 and Examples 31-33

These Examples demonstrate the beneficial effect of adding hexamethylene diamine (HMD) on the reaction temperature required for catalyst extraction. For Comparative Examples 28-30, Comparative Example 7 was repeated, but the mixing time was 20 minutes, and the temperature was varied as indicated in Table 6. For Examples 31-33, Example 11 was repeated, and the temperature was varied as indicated in Table 6.

TABLE 6

Effect of hexamethylene diamine on temperature for catalyst extraction.

| Example | Temp (° C.) | KLL | Zn/HMD |
|---|---|---|---|
| 28 | 65 | 16.76 | No HMD |
| 29 | 55 | 13.25 | No HMD |
| 30 | 45 | 8.06 | No HMD |
| 31 | 65 | 84.42 | 1.2 |
| 32 | 55 | 82.91 | 1.2 |
| 33 | 45 | 82.00 | 1.2 |

The data summarized in Table 6 represent evaluations of catalyst extraction performed at varying temperature from 45 to 65 degrees Celsius, with and without HMD present. Comparative Examples 28-30 show that catalyst extraction increases linearly with increasing temperature (represented by KLL). Examples 31-33 show that catalyst extraction does not require increased temperature when HMD is added.

Comparative Examples 34-37 and Examples 38-41

These Examples demonstrate the beneficial effect of adding hexamethylene diamine (HMD) on the mixing time required for catalyst extraction. For Comparative Examples 34-37, Comparative Example 28 was repeated, and the mixing time was varied as indicated in Table 7. For Examples 38-41, Example 11 was repeated, and the mixing time was varied as indicated in Table 7.

TABLE 7

Effect of hexamethylene diamine on mixing time required for catalyst extraction.

| Example | Mixing Time (min) | KLL | Zn/HMD |
|---|---|---|---|
| 34 | 20 | 16.13 | No HMD |
| 35 | 10 | 14.86 | No HMD |
| 36 | 5 | 14.49 | No HMD |
| 37 | 1 | 11.05 | No HMD |
| 38 | 10 | 84.42 | 1.2 |
| 39 | 5 | 114.34 | 1.2 |
| 40 | 1 | 98.24 | 1.2 |
| 41 | 0.5 | 56.23 | 1.2 |

The data summarized in Table 7 represent evaluations of catalyst extraction performed at varying mixing time from 20 minutes to 30 seconds, with and without HMD present. Examples 38-41 show that a decrease in catalyst extraction occurs when the mixing time is decreased to less than 5 minutes. Examples 38-41 show that catalyst extraction does not decrease until the mixing time is decreased to less than 1 minute, when HMD added.

Examples 42-45

These Examples demonstrate the beneficial effect of adding hexamethylene diamine (HMD) and bis-hexamethylene triamine (BHMT) to the mixing section of a mixer-settler, rather than to the feed line to this mixing section. Results are shown in Table 8.

TABLE 8

Effect of additive addition point.

| Example | Addition Point | Additive | Mixing Time | KLL | Stable Emulsion |
|---|---|---|---|---|---|
| 42 | Mixer | HMD | 20 | 23 | No |
| 43 | Mixer | BHMT | 20 | 80 | No |
| 44 | Feed Line | HMD | N/A | 14 | Yes |
| 45 | Feed Line | BHMT | N/A | 14 | Yes |

Examples 42-45 show that addition of the additives HMD or BHMT directly to the mixer system of a catalyst extraction system causes a beneficial increase in catalyst recovery, as indicated by increased KLL.

Examples 46-50

These Examples demonstrate the ability of a complex of zinc chloride ($ZnCl_2$) and bis-hexamethylene triamine (BHMT) to catalyze the cyclization of adiponitrile (ADN) to 2-cyanocyclopentylideneimine (CPI) under conditions encountered when a raffinate stream is refined to produce purified ADN.

A raffinate composition which was obtained from the tails stream of a column for removal of pentenenitriles from dinitriles (i.e. column $K'_2$ and stream 630 in FIG. 5) was used for the following examples. This raffinate had the following composition: 94% adiponitrile, 4% methylglutaronitrile, 0.1% pentenenitriles, 0.5% ethylsuccinonitrile, and 271 ppm zinc. To simulate conditions in a distillation column to distill dinitriles the raffinate was heated to 180° C.

Various additives were then added to the heated mixture. The composition of these additives is shown in Table 9.

TABLE 9

Amount of additive.

| Example | Additive | Amount of BHMT | Zn/BHMT |
|---|---|---|---|
| 46 | BHMT + $ZnCl_2$ | 1 wt % | 1 |
| 47 | BHMT + $ZnCl_2$ | 2 wt % | 0.5 |
| 48 | BHMT + $ZnCl_2$ | 0.5 wt % | 2 |
| 49 | BHMT | 2 wt % | N/A |
| 50 | $ZnCl_2$ | 0 | N/A |

In Table 9, it will be understood that the amount of BHMT is based on the total weight of the raffinate composition before addition of the additive. It will be further understood that the ratio of Zn/BHMT is expressed in terms of equivalents of Zn per mole of BHMT. The amount of $ZnCl_2$ added as per Example 50 (EX 50) was 3 wt %, based on the total weight of the raffinate composition before addition of the $ZnCl_2$.

After the addition of the additive, samples of the mixture were taken at 1 hour, 2 hours, 3 hours and 5 hours. These samples were analyzed, and the concentration of CPI in the samples was determined in terms of CPI (mol/L), i.e. moles of CPI per liter of the mixture. Results are shown in FIG. 6.

Figure 6:
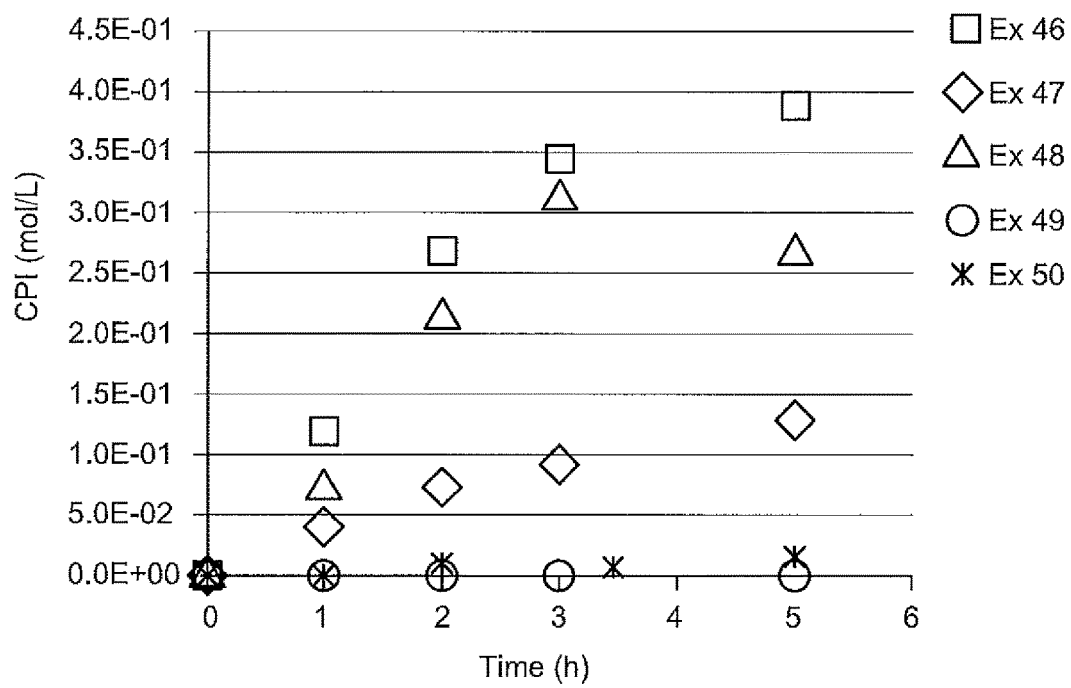
FIGS. 6 and 7 are graphs showing the conversion of adiponitrile to 2-cyanocyclopentylideneimine (CPI) in the presence of various additives over time.

FIG. 6 shows that CPI formation was negligible according to Example 49 (EX 49), wherein the additive included BHMT in the absence of $ZnCl_2$. FIG. 6 also shows that CPI formation was negligible according to Example 50 (EX 50), wherein the additive included $ZnCl_2$ in the absence of BHMT. However, FIG. 6 shows that considerable amounts of 2-cyanocyclopentylideneimine (CPI) were formed according to Examples 46-48 (EX 46 to EX 48) in increasing quantities over time when the additive included both BHMT and $ZnCl_2$.

Examples 51-53

These Examples demonstrate the ability of a complex of zinc chloride ($ZnCl_2$) and hexamethylene diamine (HMD) to catalyze the cyclization of adiponitrile (ADN) to 2-cyanocyclopentylideneimine (CPI) under conditions encountered when a raffinate stream is refined to produce purified ADN.

A raffinate material which was obtained from the tails stream of a column for removal of pentenenitriles from dinitriles (i.e. column $K'_2$ and stream 630 in FIG. 5) was used for the following examples. This raffinate had the following composition: 94% adiponitrile, 4% methylglutaronitrile, 0.1% pentenenitriles, 0.5% ethylsuccinonitrile, and 271 ppm zinc. To simulate conditions in a distillation column to distill dinitriles the raffinate was heated to 180° C.

Various additives were then added to the heated mixture. The composition of these additives is shown in Table 10.

TABLE 10

Amount of additive.

| Example | Additive | Amount of HMD | Zn/HMD |
|---|---|---|---|
| 51 | HMD + $ZnCl_2$ | 0.5 wt % | 1 |
| 52 | $ZnCl_2$ | 0 | N/A |
| 53 | HMD | 0.5 wt % | N/A |

In Table 10 it will be understood that the amount of HMD is based on the total weight of the raffinate composition before addition of the additive. It will be further understood that the ratio of Zn/HMD is expressed in terms of equivalents of Zn per mole of HMD. The amount of $ZnCl_2$ added as per Example 52 (EX 52) was 0.6 wt %, based on the total weight of the raffinate composition before addition of the $ZnCl_2$.

After the addition of the additive, samples of the mixture were taken at various times including 1 hour, 2 hours, 3 hours, 3.5 hours and 5 hours. These samples were analyzed, and the concentration of CPI in the samples was determined in terms of CPI (mol/L), i.e. moles of CPI per liter of the mixture. Results are shown in FIG. 7.

Figure 7:
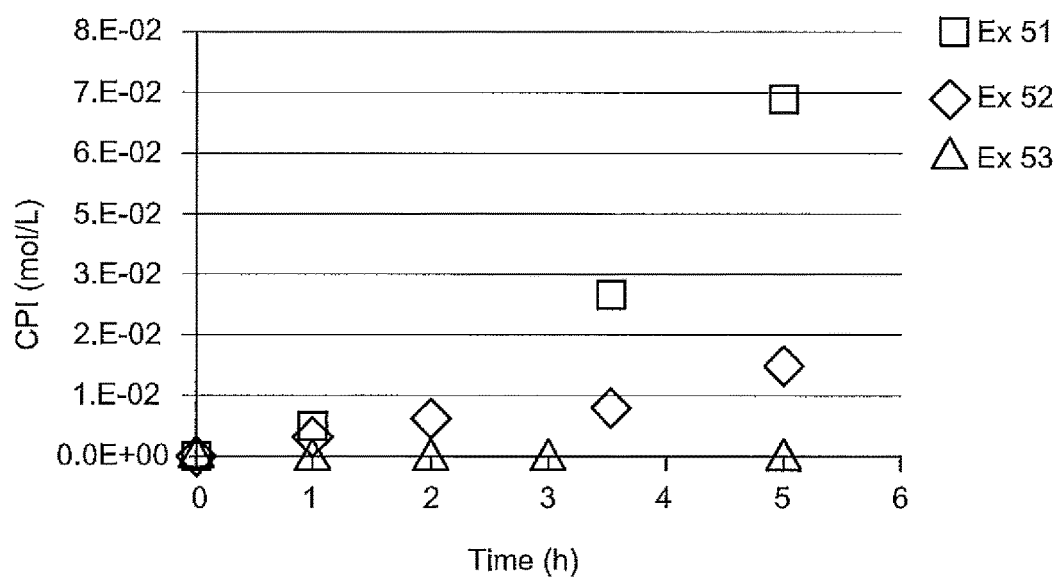

FIG. 7 shows that CPI formation was negligible according to Example 53 (EX 53), wherein the additive included HMD in the absence of $ZnCl_2$. FIG. 7 also shows that only small amounts of CPI were formed according to Example 52 (EX 52), wherein the additive included $ZnCl_2$ in the absence of HMD. However, FIG. 7 shows that considerable amounts of 2-cyanocyclopentylideneimine (CPI) were formed according to Example 51 (EX 51) in increasing quantities over time when the additive included both HMD and $ZnCl_2$, especially when the mixture was heated for 3.5 and 5 hours.

What is claimed is:

1. A process for making hexamethylene diamine (HMD), said process comprising the steps of:
   (i) introducing 3-pentenenitrile (3PN), hydrogen cyanide (HCN), zero valent nickel, at least one diphosphite-containing or diphosphonite-containing compound and a Lewis acid into a hydrocyanation reaction zone;
   (ii) maintaining the hydrocyanation reaction zone of step (i) under conditions sufficient to convert 3PN and HCN to adiponitrile (ADN);
   (iii) withdrawing a product stream from the hydrocyanation reaction zone of step (ii), wherein said product stream comprises 3PN, ADN, zero valent nickel, at least one diphosphite-containing or diphosphonite-containing compound and a Lewis acid;
   (iv) contacting at least a portion of the product stream of step (iii) with an extraction solvent to obtain a mixture of product from step (iii) and extraction solvent and maintaining this mixture under conditions to obtain a two phase mixture comprising a light phase, which comprises extraction solvent and at least one diphosphite-containing or diphosponite-containing compound, and a heavy phase, which comprises 3PN and ADN;
   (v) recovering ADN from the heavy phase from step (iv);
   (vi) reacting ADN from step (v) with hydrogen to produce hexamethylene diamine (HMD) as a product amine and at least one byproduct amine selected from the group consisting of bis-hexamethylene triamine (BHMT) and 1,2-diaminocyclohexane; and
   (vii) contacting at least one of the product amine or byproduct amines from step (vi) with product of step (iii) either before or during step (iv).

2. The process of claim 1, wherein step (vii) comprises contacting at least one of the product amine or byproduct amines from step (vi) with the product of stream of step (iii) before step (iv), followed by removing solids from the product stream prior to step (iv).

3. The process of claim 1, wherein step (vii) comprises contacting at least one of the product amine or byproduct amines from step (vi) with product of step (iii) during step (iv), followed by removing solids from the heavy phase of step (iv).

4. The process of claim 3, wherein step (v) comprises removing extraction solvent and pentenenitrile from the heavy phase of step (iv), and
   wherein solids are removed from the heavy phase after step (iv) and before extraction solvent is removed from the heavy phase.

5. The process of claim 3, wherein step (v) comprises removing extraction solvent and pentenenitrile from the heavy phase of step (iv), and
   wherein solids are removed from the heavy phase after step (iv) and before pentenenitrile is removed from the heavy phase.

6. The process of claim 1, wherein bis-hexamethylene triamine (BHMT) from step (vi) is separated from hexamethylene diamine (HMD) and 1,2-diaminocyclohexane and then contacted with product of step (iii) and extraction solvent during step (iv).

7. The process of claim 1, wherein the Lewis acid is ZnCl2.

8. The process of claim 1, wherein the catalyst comprises a diphosphite ligand of the formula:

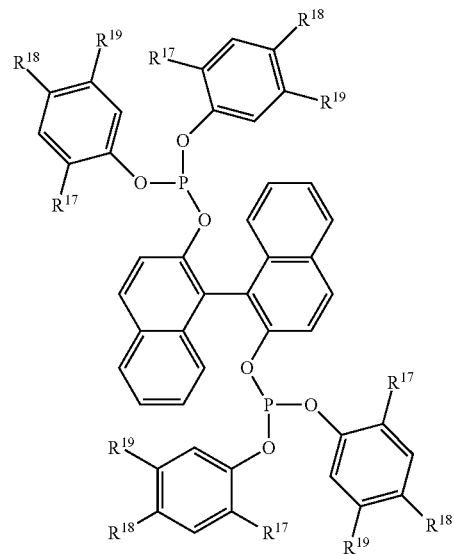

XX where R17 is selected from the group consisting of methyl, ethyl or isopropyl, and R18 and R19 are independently selected from H or methyl.

9. The process of claim 1, wherein the catalyst comprises a diphosphite ligand of the formula:

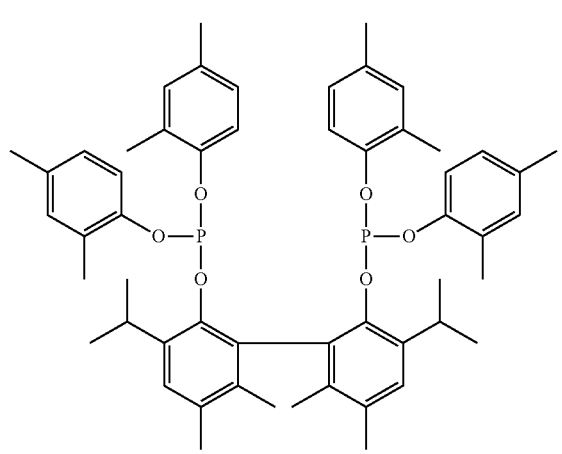

X

10. The process of claim 1, wherein at least a portion of the diphosphite-containing or diphosphonite-containing compound is complexed with zero valent Ni.

11. The process of claim 1, wherein step (iv) takes place in a multistage countercurrent liquid-liquid extractor.

12. The process of 11, wherein the first stage of the multistage countercurrent liquid-liquid extractor takes place in an extraction column.

13. The process of claim 11, wherein the first stage of the multistage countercurrent liquid-liquid extractor takes place in a mixer-settler.

14. The process of claim 13, wherein the multistage countercurrent liquid-liquid extractor comprises at least three mixer-settlers connected in series.

* * * * *